(12) United States Patent
Chen et al.

(10) Patent No.: US 11,808,147 B2
(45) Date of Patent: Nov. 7, 2023

(54) MULTI-PHASE FLUID IDENTIFICATION FOR SUBSURFACE SENSOR MEASUREMENT

(71) Applicant: Halliburton Energy Services, Inc., Houston, TX (US)

(72) Inventors: Zhonghuan Chen, Singapore (SG); Bin Dai, Katy, TX (US); Christopher Michael Jones, Katy, TX (US); Xiang Wu, Singapore (SG)

(73) Assignee: Halliburton Energy Services, Inc., Houston, TX (US)

( * ) Notice: Subject to any disclaimer, the term of this patent is extended or adjusted under 35 U.S.C. 154(b) by 192 days.

(21) Appl. No.: 17/481,165

(22) Filed: Sep. 21, 2021

(65) Prior Publication Data

US 2023/0097490 A1    Mar. 30, 2023

(51) Int. Cl.
  *E21B 49/08* (2006.01)
  *G01N 33/24* (2006.01)
  *G01V 8/02* (2006.01)

(52) U.S. Cl.
  CPC ......... *E21B 49/081* (2013.01); *G01N 33/241* (2013.01); *G01V 8/02* (2013.01)

(58) Field of Classification Search
  CPC ....... E21B 49/081; G01N 33/241; G01V 8/02
  See application file for complete search history.

(56) References Cited

U.S. PATENT DOCUMENTS

| 10,927,672 B2 | 2/2021 | Dai et al. |
| 2010/0192684 A1 | 8/2010 | Wu et al. |
| 2011/0023594 A1 | 2/2011 | Pelletier et al. |
| 2013/0213149 A1 | 8/2013 | Boe et al. |
| 2014/0110105 A1 | 4/2014 | Jones et al. |
| 2014/0195215 A1 | 7/2014 | Chen et al. |

(Continued)

FOREIGN PATENT DOCUMENTS

| WO | 2017-129738 | 8/2017 | |
| WO | WO-2017129738 A1 * | 8/2017 | ............. E21B 47/10 |

OTHER PUBLICATIONS

International Search Report and Written Opinion for Application No. PCT/US2021/054428, dated May 26, 2022.

*Primary Examiner* — Michael J Dalbo
*Assistant Examiner* — Kaleria Knox
(74) *Attorney, Agent, or Firm* — John Wustenberg; C. Tumey Law Group PLLC

(57) ABSTRACT

A method and a system for measuring downhole fluid properties. The downhole fluid sampling tool may comprise at least one probe and at least one passageway that passes through the at least one probe and into the downhole sampling tool. The method may comprise drawing a wellbore fluid through the at least one probe and through the at least one passageway, obtaining a first channel measurement of the wellbore fluid, obtaining at least a second channel measurement, clustering channel data from a plurality of channel measurements comprising the first channel measurement and the at least second channel measurement, and measuring a phase through a plurality of channels. The method may further comprise separating a plurality of phase signals based on the phase measured through the plurality of channels, labeling the wellbore fluid, assigning the plurality of phase signals to specific phases of a multi-phase fluid, and estimating a fluid property.

17 Claims, 11 Drawing Sheets

(56) References Cited

U.S. PATENT DOCUMENTS

| | | |
|---|---|---|
| 2014/0306096 A1 | 10/2014 | Freese et al. |
| 2015/0377776 A1 | 12/2015 | Xie |
| 2019/0017377 A1 | 1/2019 | He et al. |
| 2019/0100995 A1 | 4/2019 | He et al. |
| 2019/0162066 A1 | 5/2019 | Chen et al. |
| 2019/0353632 A1 | 11/2019 | Pelletier et al. |
| 2020/0240264 A1 | 7/2020 | He et al. |
| 2020/0284140 A1 | 9/2020 | Jones et al. |
| 2020/0378250 A1 | 12/2020 | Olapade et al. |
| 2020/0400017 A1 | 12/2020 | Olapade et al. |
| 2020/0400858 A1 | 12/2020 | Olapade et al. |
| 2021/0047924 A1* | 2/2021 | Kallehbasti ............ E21B 49/10 |
| 2021/0054737 A1 | 2/2021 | Dai et al. |
| 2021/0071522 A1 | 3/2021 | Dai et al. |
| 2021/0088447 A1 | 3/2021 | Stark et al. |
| 2021/0110246 A1 | 4/2021 | Chen et al. |
| 2021/0131951 A1 | 5/2021 | Dai et al. |
| 2021/0207478 A1 | 7/2021 | Pelletier et al. |
| 2021/0215033 A1 | 7/2021 | Jones et al. |
| 2021/0231001 A1 | 7/2021 | Jones et al. |
| 2021/0239000 A1 | 8/2021 | Olapade et al. |

\* cited by examiner

MULTI-PHASE FLUID IDENTIFICATION FOR SUBSURFACE SENSOR MEASUREMENT

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation.

One technique for collecting relevant information involves obtaining and analyzing fluid samples from a reservoir of interest. There are a variety of different tools that may be used to obtain the fluid sample. The fluid sample may then be analyzed to determine fluid properties, including, without limitation, component concentrations, plus fraction molecular weight, gas-oil ratios, bubble point, dew point, phase envelope, viscosity, combinations thereof, or the like. Conventional analysis has required transfer of the fluid samples to a laboratory for analysis. Downhole analysis of the fluid sample may also be used to provide real-time fluid properties, thus augmenting laboratory measurements and also providing information mitigating delays associated with laboratory analysis. In addition, downhole fluid analysis may be acquired at more physical locations along the wellbore than may be sampled in the same amount of time. Further, downhole fluid analysis may improve or optimize the sampling operation.

Formation fluid flow often comprises multiple phases. Accurate determination of fluid properties of one of the component phases may be problematic in the presence of multiple phases. One such property is the analysis of contamination of the formation fluid with drilling fluids components, such as drilling fluid filtrate. In fact, drilling fluid filtrate may be the source of a multiple phase. Fluid samples having drilling fluid contamination, whether miscible and mixed into the oil phase or immiscibly present as a separate phase from the formation fluid, may result in non-representative fluids and measured properties. Techniques to determine drilling fluid contamination may include use of pump-out curves, such as density, gas-to-oil ratio, and resistivity, among other properties of the fluids. Moreover, a dynamic measurement of subsurface optical spectra may meet one phase on some optical channels, and another phase on some other optical channels. Identifying specific fluid phases plays a significant role for fluid ratio estimation and pure formation fluid signature extraction.

BRIEF DESCRIPTION OF THE DRAWINGS

These drawings illustrate certain aspects of some of the embodiments of the present invention, and should not be used to limit or define the invention.

DETAILED DESCRIPTION

Figure 1:
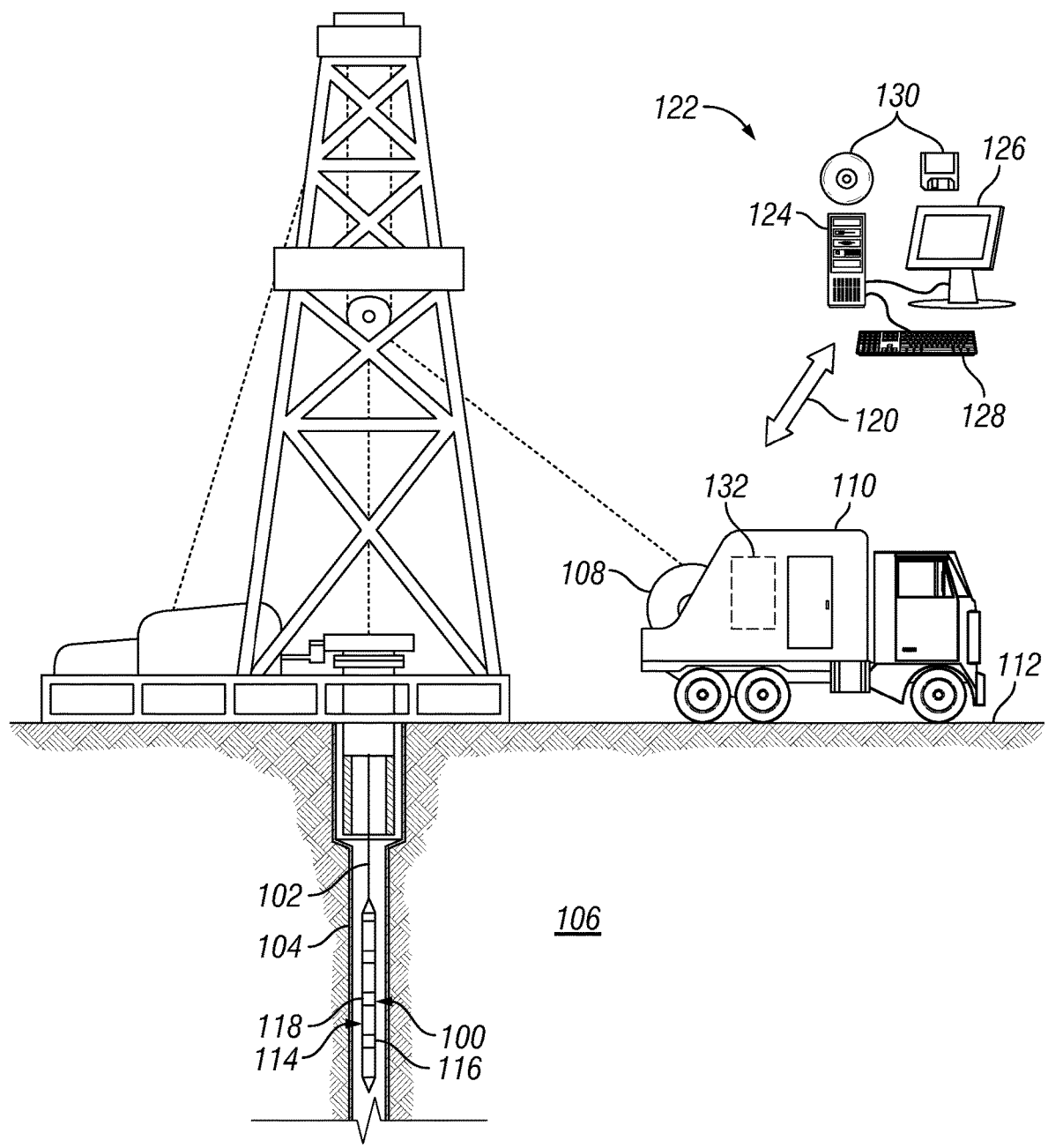
FIG. 1 is a schematic diagram of an example downhole fluid sampling tool on a wireline.

Downhole sampling is a downhole operation that may be used for formation evaluation, asset decisions, and operational decisions. Estimation of pure filtrate readings are important to the estimation of filtrate contamination of formation fluid which in turn is important for successfully executing downhole sampling operations. As currently practiced, pure mud filtrate properties may be assumed or estimated for the purpose of deriving sample contamination. A measurement of the response of sensors to pure filtrate may be hampered by the length of time it takes to remove particles from an inlet flow line, such that by the time the particles clear, the sample may no longer comprise pure filtrate. Extrapolation of readings to determine an initial fluid composition as a function of time, volume, or dependent variable therein, such as pure filtrate determination may be practiced, but the results may not be reliable due to the high degree of uncertainty. The methods and apparatus disclosed herein may be presented for the separation and identification of multiphase fluids.

As disclosed herein, a method for measuring downhole fluid properties may comprise disposing a downhole fluid sampling tool into a wellbore, wherein the downhole fluid sampling tool may comprise: at least one probe configured to fluidly connect the downhole fluid sampling tool to a formation in the wellbore, wherein the at least one probe may comprise at least one fluid sensor; and at least one passageway, wherein the at least one passageway may pass through the at least one probe and into the downhole sampling tool, wherein the at least one fluid sensor may be fluidly connected to the formation through the at least one probe. The method may further comprise drawing a wellbore fluid through the at least one probe and through the at least one passageway, proximal to the at least one fluid sensor, such that the fluid sensor may make a first channel measurement on the fluid sample; and obtaining at least a second channel measurement on the fluid sample from the at least one fluid sensor. The method may further comprise clustering channel data from a plurality of channel measurements, wherein the plurality of channel measurements may comprise the first channel measurement and the at least second channel measurement on the fluid sample; measuring a phase through the plurality of channels; and separating a plurality of phase signals based on the phase measured through the plurality of channels. The method may further comprise labeling the fluid, wherein the labeling may comprise analyzing the plurality of phase signals and assigning the plurality of phase signals to specific phases of a multiphase fluid; and estimated a fluid property.

The multiphase nature of the fluids may be from aqueous formation fluid, aqueous drilling fluid filtrate, formation fluid gas, formation fluid oil, or oil-based filtrate. Filtrate is the liquid portion of a drilling fluid. These components may be present in combinations that yield multi-phase. Further, some drilling fluids, such as emulsions, may contain both oil and aqueous components. Hence, in order to derive the influence of the filtrate, the aqueous portion and the organic portion must be known.

As disclosed herein, a property of a fluid refers to a chemical property, phase property, i.e., fluid (liquid aqueous, liquid organic, or gas), or solid phase in concentration or identification, or phase behavior. Examples of properties may include, compositional component concentrations, such as methane, ethane, propane, butane, and pentane; organic liquid components, such as a hexane plus (C6+) fraction or hydrocarbon components therein, saturates fraction, aromatics fraction, resins fraction, asphaltenes fraction; total acid number; pH; eH (activity of electrons); water composition, including cations such as sodium, potassium, calcium, magnesium and trace cations, anions such as chloride, bromide, sulfide, sulfate, carbonate, bicarbonate, other dissolved solids; organic acids and/or their conjugates; and other inorganic components such as carbon dioxide, hydrogen sulfide, nitrogen or water. Physical properties may include compressibility, density, thermal conductivity, heat capacity, viscosity; phase behavior including bubble point, gas to oil ratio, phase envelope for gas-liquid or solid-liquid, including asphaltenes or waxes; and compositional grading with depth. Properties may also include the interpretation of similarity or differences between different set fluids such as that reflected by reservoir or field architecture, and reservoir compartmentalization. Properties may be used therein to obtain reservoir or field architecture or reservoir compartmentalization, compositional grading, and may be used to interpreted processes leading to various compositional grading or other equilibrium or disequilibrium distributions of fluids and fluid properties. Properties shall therefore refer to the measured, calculated, and inferred properties obtained from sensor measurements and the properties derived from other therein such as but not limited to that by interpretation, such as equation of state interpretation.

For example, the methods and apparatus disclosed herein may identify the phases of each dominating fluid for each channel. The methods and apparatus disclosed herein may further identify pure phase channel observations versus mixed phase channel observations. Identifying the fluid type or fluid phase on a per channel basis may further benefit the estimation of fluid phase ratios or concentrations; the assessment of mud contamination; the construction of pure signature for the formation fluids; and the producible water cut of a zone, including, but not limited to, a transition zone in which both formation oil and formation water is simultaneously sampled.

A method of fluid identification may comprise clustering a plurality of channels to automatically classify an observed optical or non-optical spectrum into different fluid groups. The methods may also comprise fluid labeling of each of the fluid groups, wherein the fluid labeling may be guided by the observation of a deterministic or probabilistic sensor channel which responds characteristically to different phases such as density sensor channel observations. After completion of the fluid labeling step, a fluid ratio estimation and a fluid signature extraction may be determined. Essentially, fluid ratio estimation and fluid signature estimation may be determined or extracted by grouping such as but not limited to clustering and labeling fluids based on the characteristic channel observation such as but not limited to the density observation.

Conventional methods may depend on pre-processing of the observed channel responses such as but not limited to optical data responses, such as debiasing and normalization. By contrast, the grouping methods such as but not limited to clustering methods disclosed herein may depend on a distribution such as a statistical distribution, rather than exclusively an amplitude bias or scaling as in conventional methods. The grouping methods such as clustering methods disclosed herein present a more robust method for fluid identification. The fluid labeling method disclosed herein may improve fluid classification performance by sharing information between at least two paired channels of at least one sensor. Cross sensor channel paring is also possible. Moreover, the fluid labeling methods disclosed herein may improve the accuracy of channel pairs of low separability by importing guiding information such as observed density, capacitance, resistivity, and acoustic information.

During formation tester pump outs, reservoir fluids are often multi-phase flow including slug flow, dispersed flow and emulsion flow, which may present difficulties in measuring combinations of liquids (water and oil) and gases or in some cases solids as well. It may be desirable to measure the physical and chemical properties of the individual phases of the fluids. The reservoir fluid compositions and distributions provide important information for field engineers to make decisions on field development. Accurate gas composition may also assist in decision making regarding the installation of expensive production facilities. By directly measuring the sensor responses such as light-absorption responses for optical sensors of compositions in fluid samples, for instance optical measurement may provide an approach for fluid identification, composition analysis, and physical and chemical properties analysis.

The fluid samples may be measured either in a laboratory environment or in a real time subsurface borehole. Downhole fluid samples need not be captured in a container for analysis. Hence, as disclosed herein, the subsurface sensor channel measurements will be embodied by optical spectroscopy channels and a density sensor channel, but the embodiment is not exclusive to these sensors or channels. Optical sensor channel analysis may provide real-time information fluids at the field subsurface pressure and temperature. Other sensors with at least one channel include resistivity sensors, capacitance sensors, acoustic sensors, chromatographic sensors, microfluidic sensors, phase behavior sensors including but not limited to compressibility sensors and bubble point sensors, electrochemical sensors, mass spectrometer or mass spectroscopy sensors. More importantly, in the field the reservoir compositional variations may be directly mapped with greater spatial resolution than may otherwise be available, based on the number of samples which may be acquired downhole and sent to a laboratory. An in-situ compositional analysis may be combined with a spatial mapping of compositional properties and may provide an improved basis for selecting the locations from which to sample fluids for laboratory analysis. Moreover, the sample quality, as it is being withdrawn from a reservoir, may be quantified in terms of aliquot representation of the formation fluid in the reservoir and contamination levels of drilling fluid filtrate.

In some embodiments, it should be noted that only limited sensor channels such as optical channels may be implemented in subsurface optical spectroscopy. For example, the optical spectra of fluid samples may be measured channel by channel dynamically. In other examples, multiple channels may be acquired simultaneously, but at different locations. In other examples, a viewing window of the channels may oscillate between phases or a combination of phases therein and may provide difficult temporal analysis of the fluid's physical and chemical behavior.

For example, the fluid's chemical behavior may include, but may not limited to, a petroleum composition comprising saturates, aromatics, resins, asphaltenes fractions, methane, ethane, propane, butane, pentane, hexane and higher components and individual or lumped higher hydrocarbon components (where lumping may be the composite analysis or reporting of two or more hydrocarbon components), inorganic component composition, including water, nitrogen, carbon dioxide, and hydrogen sulfide chemical potential, including, but not limited to, reactive capability acidic levels of individual components, i.e., organic acids, or as a whole, i.e., pH or total acid number (TAN), or for instance redox potential. These chemical properties may be directly probed optically, by optical analysis in combination with other measurement devices, which may include, but may not be limited to, density, bubble point, compressibility, acoustic, NMR, capacitance, dielectric spectroscopy, nuclear methods, x-ray methods, terahertz methods, and resistivity.

Alternatively, chemical properties may be interpreted based on physical, chemical, or empirical models as a secondary interpretation based on the directly probed chemical properties, which may include but may not be limited to the listed methods. For example, physical properties may include, but may not limited to, bubble point, compressibility, phase envelope, density, and viscosity, and may be measured directly by devices such as density sensors, viscometers, phase behavior experimentation, trapped volume devices, fractionation devices such as valved devices or membrane devices or derived by physical, chemical, or empirical models as a secondary interpretation based on directly probed physical properties. Physical properties may be measured or derived based, in part, on multiple measurements. As a non-limiting example for instance, phase behavior (or other physical properties), like compressibility or bubble point may be derived based on combinations of physical measurements and compositions as modeled by an equation of state (EOS) such as, but not limited to, as Peng Robertson or SRK cubic equation of state, a viral equation of state, or a PC-SAFT equation of state or an empirical machine learning model such as, but not limited to a neural network or a random forest model or a gradient boost method. Multiphase fluids provide difficulties for interpretation.

During a subsurface optical measurement, sampled formation fluids may be together with some single phase or multiphase mud contaminations, flow through the sampling path. Alternatively, multiphase fluids may flow through the sampling path directly from multiphase formation fluids. Alternatively, multiphase fluids may be induced from phase changes due to pressure, volume, or temperature perturbations during sampling. In some examples, the sampled fluids for different channels may be distributed in space or time, such as channels configured in a rotating wheel positioned in an optical path of a fluid phase detector. However, as disclosed herein, the fluids may be sampled temporally by using a rotating wheel, wherein the fluids may be assumed to be the same phase (single-phase assumption). Consequently, obtaining the pure signature for the formation fluids and the mud filtrate may prove problematic, yielding errors for water/hydrocarbon ratio estimation and mud contamination assessment.

The present disclosure provides methods and apparatus for identifying the phases of dominating fluid for each channel, and further for identifying pure phase channel observations versus mixed phase channel observations. Identifying the fluid type on a per channel basis may further benefit the following: a) the estimation of fluid phase ratios or concentrations; b) the assessment of mud contamination; c) the construction of pure signature for the formation fluids; d) the producible water cut of a zone, including but not limited to, a transition zone; and e) the measurement of fluid properties for at least one of the inherent sample phases (oil, water, gas, solid).

FIG. 1 is a schematic diagram of downhole fluid sampling tool 100 on a conveyance 102. As illustrated, wellbore 104 may extend through subterranean formation 106. In examples, reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run downhole fluid sampling tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Downhole fluid sampling tool 100 may be suspended in wellbore 104 on conveyance 102. Other conveyance types may be used for conveying downhole fluid sampling tool 100 into wellbore 104, including coiled tubing and wired drill pipe, conventional drill pipe for example. Downhole fluid sampling tool 100 may comprise a tool body 114, which may be elongated as shown on FIG. 1. Tool body 114 may be any suitable material, including without limitation titanium, stainless steel, alloys, plastic, combinations thereof, and the like. Downhole fluid sampling tool 100 may further include one or more sensors 116 for measuring properties of the fluid sample, reservoir fluid, wellbore 104, subterranean formation 106, or the like. In examples, downhole fluid sampling tool 100 may also include a fluid analysis module 118, which may be operable to process information regarding fluid sample, as described below. The downhole fluid sampling tool 100 may be used to collect fluid samples from subterranean formation 106 and may obtain and separately store different fluid samples from subterranean formation 106.

In examples, fluid analysis module 118 may comprise at least one a sensor that may continuously monitor a reservoir fluid. Such sensors include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors. Sensors may measure a contrast between drilling fluid filtrate properties and formation fluid properties. Fluid analysis module 118 may be operable to derive properties and characterize the fluid sample. By way of example, fluid analysis module 118 may measure absorption, transmittance, or reflectance spectra and translate such measurements into component concentrations of the fluid sample, which may be lumped component concentrations, as described above. The fluid analysis module 118 may also measure gas-to-oil ratio, fluid composition, water cut, live fluid density, live fluid viscosity, formation pressure, and formation temperature. Fluid analysis module 118 may also be operable to determine fluid contamination of the fluid sample and may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 118 may include random access memory (RAM), one or more processing units, such as a central processing unit (CPU), or hardware or software control logic, ROM, and/or other types of nonvolatile memory.

Any suitable technique may be used for transmitting phase signals from the downhole fluid sampling tool 100 to the surface 112. As illustrated, a communication link 120 (which may be wired or wireless, for example) may be provided that may transmit data from downhole fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. The information handling system 122 may act as a data acquisition system and possibly a data processing system that analyzes information from downhole fluid sampling tool 100. For example, information handling system 122 may process the information from downhole fluid sampling tool 100 for determination of fluid contamination. The information handling system 122 may also determine additional properties of the fluid sample (or reservoir fluid), such as component concentrations, pressure-volume-temperature properties (e.g., bubble point, phase envelop prediction, etc.) based on the fluid characterization. This processing may occur at surface 112 in real-time. Alternatively, the processing may occur downhole hole or at surface 112 or another location after recovery of downhole fluid sampling tool 100 from wellbore 104. Alternatively, the processing may be performed by an information handling system in wellbore 104, such as fluid analysis module 118. The resultant fluid contamination and fluid properties may then be transmitted to surface 112, for example, in real-time.

Figure 2:
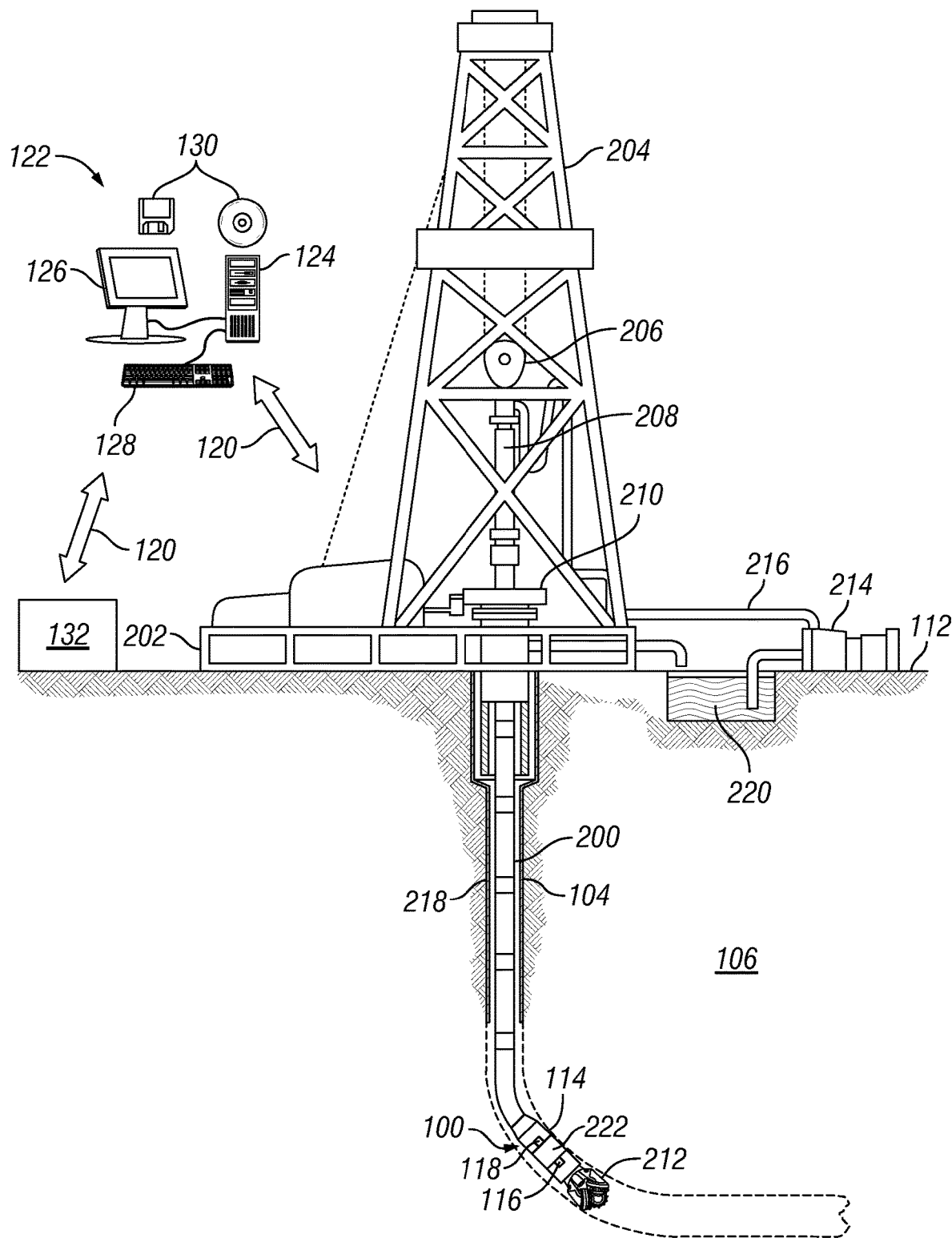
FIG. 2 is a schematic diagram of an example downhole fluid sampling tool on a drill string.

Referring now to FIG. 2, a schematic diagram of downhole fluid sampling tool 100 disposed on a drill string 200 in a drilling operation. Downhole fluid sampling tool 100 may be used to obtain a fluid sample, for example, a fluid sample of a reservoir fluid from subterranean formation 106. The reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. Without limitation, drill bit 212 may include, roller cone bits, PDC bits, natural diamond bits, any hole openers, reamers, coring bits, and the like. As drill bit 212 rotates, it may create and extend wellbore 104 that penetrates various subterranean formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and downhole fluid sampling tool 100. Downhole fluid sampling tool 100, which may be built into the drill collars 222 may gather measurements and fluid samples as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Downhole fluid sampling tool 100 may be similar in configuration and operation to downhole fluid sampling tool 100 shown on FIG. 1 except that FIG. 2 shows downhole fluid sampling tool 100 disposed on drill string 200. Alternatively, the sampling tool may be lowered into the wellbore after drilling operations on a wireline.

Downhole fluid sampling tool 100 may further include one or more sensors 116 for measuring properties of the fluid sample reservoir fluid, wellbore 104, subterranean formation 106, or the like. The properties of the fluid are measured as the fluid passes from the formation through the tool and into either the wellbore or a sample container. As fluid is flushed in the near wellbore region by the mechanical pump, the fluid that passes through the tool generally reduces in drilling fluid filtrate content, and generally increases in formation fluid content. The downhole fluid sampling tool 100 may be used to collect a fluid sample from subterranean formation 106 when the filtrate content has been determined to be sufficiently low. Sufficiently low depends on the purpose of sampling. For some laboratory testing below 10% drilling fluid contamination is sufficiently low, and for other testing below 1% drilling fluid filtrate contamination is sufficiently low. Sufficiently low also depends on the nature of the formation fluid such that lower requirements are generally needed, the lighter the oil as designated with either a higher GOR or a higher API gravity. Sufficiently low also depends on the rate of cleanup in a cost benefit analysis since longer pumpout times required to incrementally reduce the contamination levels may have prohibitively large costs. As previously described, the fluid sample may comprise a reservoir fluid, which may be contaminated with a drilling fluid or drilling fluid filtrate. Downhole fluid sampling tool 100 may obtain and separately store different fluid samples from subterranean formation 106 with fluid analysis module 118. Fluid analysis module 118 may operate and function in the same manner as described above. However, storing of the fluid samples in the downhole fluid sampling tool 100 may be based on the determination of the fluid contamination. For example, if the fluid contamination exceeds a tolerance, then the fluid sample may not be desired to be stored. If the fluid contamination is within a tolerance, then the fluid sample may be stored in the downhole fluid sampling tool 100.

As previously described, information from downhole fluid sampling tool 100 may be transmitted to an information handling system 122, which may be located at surface 112. As illustrated, communication link 120 (which may be wired or wireless, for example) may be provided that may transmit data from downhole fluid sampling tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations to estimate clean fluid composition.

Figure 3:
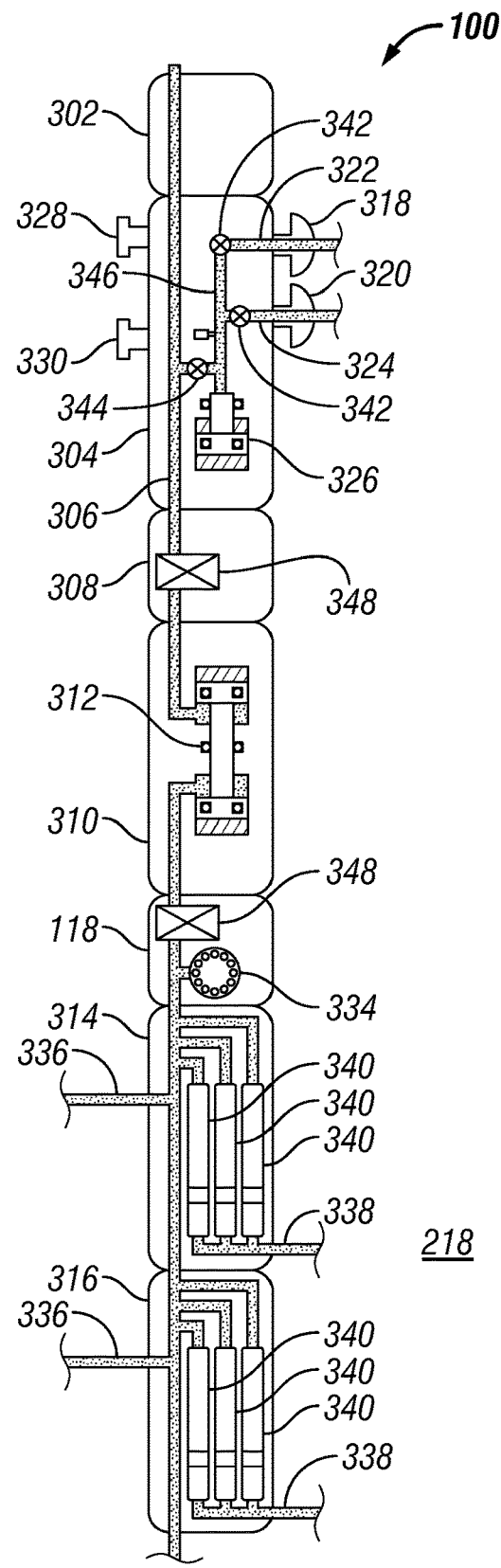
FIG. 3 is a schematic diagram of a downhole fluid sampling tool with a filter disposed in a chamber.

FIG. 3 is a schematic of downhole fluid sampling tool 100. In examples one embodiment, the downhole fluid sampling tool 100 includes a power telemetry section 302 through which the tool communicates with other actuators and sensors 116 in drill string 200 or conveyance 102 (e.g., referring to FIGS. 1 and 2), the drill string's telemetry section 302, and/or directly with a surface telemetry system (not illustrated). In examples, power telemetry section 302 may also be a port through which the various actuators (e.g., valves) and sensors (e.g., temperature and pressure sensors) in the downhole fluid sampling tool 100 may be controlled and monitored. In examples, power telemetry section 302 includes a computer that exercises the control and monitoring function. In one embodiment, the control and monitoring function is performed by a computer in another part of the drill string or wireline tool (not shown) or by information handling system 122 on surface 112 (e.g., referring to FIGS. 1 and 2).

In examples, downhole fluid sampling tool 100 includes a dual probe section 304, which extracts fluid from the reservoir and delivers it to a passageway 306 that extends from one end of downhole fluid sampling tool 100 to the other. Without limitation, dual probe section 304 includes two probes 318, 320 which may extend from downhole fluid sampling tool 100 and press against the inner wall of wellbore 104 (e.g., referring to FIG. 1). Probe channels 322, 324 may connect probes 318, 320 to passageway 306. The high-volume bidirectional pump 312 may be used to pump fluids from the reservoir, through probe channels 322, 324 and to passageway 306. Alternatively, a low volume pump 326 may be used for this purpose. Two standoffs or stabilizers 328, 330 hold downhole fluid sampling tool 100 in place as probes 318, 320 press against the wall of wellbore 104. In examples, probes 318, 320 and stabilizers 328, 330 may be retracted when downhole fluid sampling tool 100 may be in motion and probes 318, 320 and stabilizers 328, 330 may be extended to sample the formation fluids at any suitable location in wellbore 104. Other probe sections include focused sampling probes, oval probes, or packers.

In examples, passageway 306 may be connected to other tools disposed on drill string 200 or conveyance 102 (e.g., referring to FIGS. 1 and 2). In examples, downhole fluid sampling tool 100 may also include a quartz gauge section 308, which may include sensors to allow measurement of properties, such as temperature and pressure, of fluid in passageway 306. Additionally, downhole fluid sampling tool 100 may include a flow-control pump-out section 310, which may include a high-volume bidirectional pump 312 for pumping fluid through passageway 306. In examples, downhole fluid sampling tool 100 may include two multi-chamber sections 314, 316, referred to collectively as multi-chamber sections 314, 316 or individually as first multi-chamber section 314 and second multi-chamber section 316, respectively.

In examples, multi-chamber sections 314, 316 may be separated from flow-control pump-out section 310 by sensor section 332, which may house at least one non-optical fluid sensor 348 and/or at least optical measurement tool 334. It should be noted that non-optical fluid sensor 348 and optical measurement tool 334 may be disposed in any order on passageway 306. Additionally, although depicted in sensor section 332. Both non-optical fluid sensor 348 and optical measurement tool 334 may be disposed along passageway 306 at any suitable location within downhole fluid sampling tool 100.

Non-optical fluid sensor 348 may be displaced within sensor section 332 in-line with passageway 306 to be a "flow through" sensor. In alternate examples, non-optical fluid sensor 348 may be connected to passageway 306 via an offshoot of passageway 306. Without limitation, optical measurement tool 334 may include but not limited to the density sensor, capacitance sensor, resistivity sensor, and/or combinations thereof. In examples, non-optical fluid sensor 348 may operate and/or function to measure fluid properties of drilling fluid filtrate.

Optical measurement tool 334 may be displaced within sensor section 332 in-line with passageway 306 to be a "flow through" sensor. In alternate examples, optical measurement tool 334 may be connected to passageway 306 via an offshoot of passageway 306. Without limitation, optical measurement tool 334 may include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors, microfluidic sensors, selective electrodes such as ion selective electrodes, and/or combinations thereof. In examples, optical measurement tool 334 may operate and/or function to measure drilling fluid filtrate, discussed further below.

Additionally, multi-chamber section 314, 316 may comprise access channel 336 and chamber access channel 338. Without limitation, access channel 336 and chamber access channel 338 may operate and function to either allow a solids-containing fluid (e.g., mud) disposed in wellbore 104 in or provide a path for removing fluid from downhole fluid sampling tool 100 into wellbore 104. As illustrated, multi-chamber section 314, 316 may comprise a plurality of chambers 340. Chambers 340 may be sampling chamber that may be used to sample wellbore fluids, formation fluids, and/or the like during measurement operations.

During downhole measurement operations, a pumpout operation may be performed. A pumpout may be an operation where at least a portion of a fluid which may contain solids—(e.g., drilling fluid, mud, filtrate etc.) may move through downhole fluid sampling tool 100 until substantially increasing concentrations of formation fluids enter downhole fluid sampling tool 100. For example, during pumpout operations, probes 318, 320 may be pressed against the inner wall of wellbore 104 (e.g., referring to FIG. 1). Pressure may increase at probes 318, 320 due to compression against the formation 106 (e.g., referring to FIG. 1 or 2) exerting pressure on probes 318, 320. As pressure rises and reaches a predetermined pressure, valves 342 opens so as to close equalizer valve 344, thereby isolating fluid passageway 346 from the annulus 218. In this manner, valve 342 ensures that equalizer valve 344 closes only after probes 318, 320 has entered contact with mud cake (not illustrated) that is disposed against the inner wall of wellbore 104. In examples, as probes 318, 320 are pressed against the inner wall of wellbore 104, the pressure rises and closes the equalizer valve in fluid passageway 346, thereby isolating the fluid passageway 346 from the annulus 218. In this manner, the equalizer valve in fluid passageway 346 may close before probes 318, 320 may have entered contact with the mud cake that lines the inner wall of wellbore 104. Fluid passageway 346, now closed to annulus 218, is in fluid communication with low volume pump 326.

As low volume pump 326 is actuated, formation fluid may thus be drawn through probe channels 322, 324 and probes 318, 320. The movement of low volume pump 326 lowers the pressure in fluid passageway 346 to a pressure below the formation pressure, such that formation fluid is drawn through probe channels 322, 324 and probes 318, 320 and into fluid passageway 346. Probes 318, 320 serves as a seal to prevent annular fluids from entering fluid passageway 346. Such an operation as described may take place before, after, during or as part of a sampling operation.

Next, high-volume bidirectional pump 312 activates and equalizer valve 344 is opened. This allows for formation fluid to move toward high-volume bidirectional pump 312 through passageway 306. Formation fluid moves through passageway 306 to sensor section 332. Once the drilling fluid filtrate has moved into sensor section 332 high-volume bidirectional pump 312 may stop. This may allow the drilling fluid filtrate to be measured by optical measurement tool 334 within sensor section 332. Without limitation, any suitable properties of the formation fluid may be measured. Other pumps may be used such as centrifugal pumps, siphon pumps, or even underbalanced actuation of natural fluid flow such as but not limited to drill stem testing operations or underbalanced drilling operations, or managed pressure operations.

Figure 4:
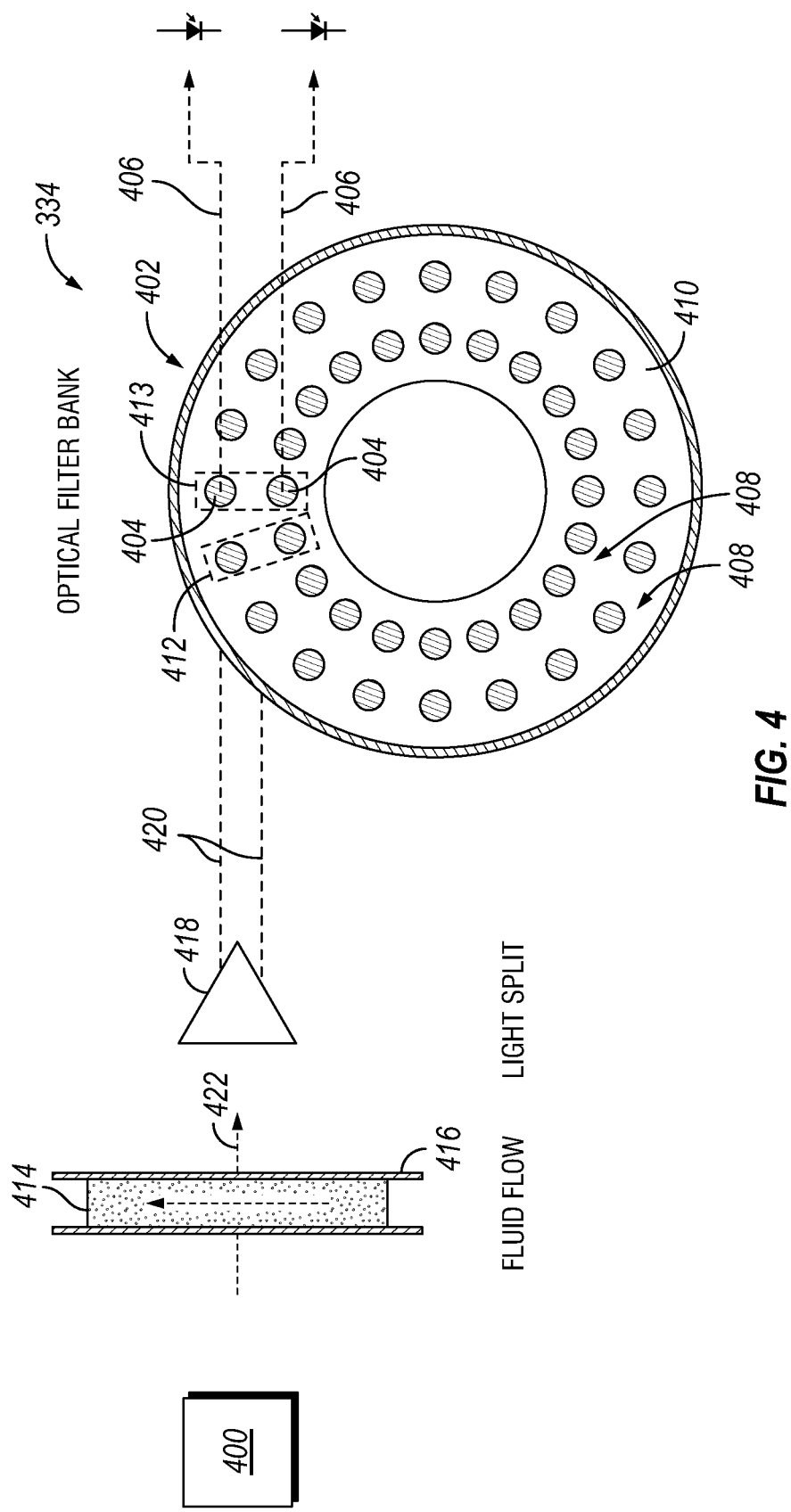
FIG. 4 depicts a hardware configuration of a dynamic subsurface optical measurement tool.

FIG. 4 depicts a hardware configuration of a dynamic subsurface optical measurement tool 334. It should be note that a channel, disclosed herein, may be a measurement of the light transmittance through an optical filter. Optical measurement tool 334 may include a light source 400, a filter bank 402 comprising a plurality of optical filters 404 (measurement of the light transmittance through an optical filter 406 is called a channel 406) configured as two rings 408 on optical plate 410, within a channel pair 412 on each azimuth. It should be noted that each channel 406 may be designed, based on the construction of each channels 406 respective optical filter 406, to measured different properties of fluid 414. During the rotation of optical plate 410, the two optical filters 404 on a channel pair 412 may be synchronized spatially or in time to measure substantially the same fluid 414 in glass pipe 416. As discussed below, and illustrated in FIG. 4, an active channel pair 413 is a channel pair 412 in which optical measurements are being taken to form one or more channels 406. In some embodiments, channel pairs 412 may be near synchronized such that channel pairs 412 have a sufficient probability of observing the same phase, i.e., better than 10% but more desirably more than 50% and yet more desirably more than 80%. In other embodiments, more than two channels 406 may be sufficiently synchronized according to a desired probability of observing a single phase in time or space. A velocity calculation of the fluid phase specific velocities may be used to aid synchronization over longer distances, or time. Alternatively, distribution calculations, or autocorrelation calculations may be used to improve the synchronization over longer distances or time. If the channels are sufficiently close in distance or time, the channel signals may not need additional efforts of synchronization. During measurement, fluid samples 414 (which is formation fluid from passageway 306) may flow through a viewing region as a non-limiting example constructed by a set of windows or other transparent region of the flow path. Alternatively, the viewing region or viewing area might not be transparent to visible light but rather to the form of energy used to measure the fluid characteristics for a given sensor. As such a viewing region or area for an acoustic sensor would ideally have a low acoustic impedance even if it is not transparent to visible light. Alternatively, the viewing region or area may be transparent (i.e., pass energy with low attenuation) to infrared light, or magnetic fields instead of visible light. In some embodiments for some sensors, the viewing region 408 or area is more generally a measurement region 408 or area as is the case with some phase behavior sensors or some density sensors. In examples, viewing region 408 may be at least a part of passageway 306 and/or a branch off of passageway 306). In one nonlimiting embodiment, light 418 absorbed by fluid sample 414 may be split into at least two ray paths 420. Split light rays 420 may be measured by detectors, not shown, as they pass through channel pair 412 separately. Filter bank 402 may rotate to another channel pair 412 after the measurement of each channel 406 from channel pair 412 and may dynamically gather an optical spectra measurement of all channels after a full sampling channel rotation. It should be noted, the methods disclosed herein may not be limited in simultaneous measurements of a channel pair 412 (two optical filters 414 and their respective channel 406) but may also apply to cases with one or more optical filters 414 or filter banks 402, at least one channel 406, or, alternatively, two or more channels 406. Mixed sensor types may also be utilized such as but not limited to a density channel with an optical channel.

Generally, in conventional interpretations of optical analysis, fluid sample 414 may keep a consistent or same fluid phase during each of a ten-second measurement circle. Fluid sample 414 may comprise a mixture of hydrocarbons and water, gas, or solids, especially in the case of water-based-mud), and also in transition zone sampling or sampling below the saturation pressure of a liquid for which gas evolves. Generally, fluid sample 414 may flow through flow path 422 of light 418 and into an active channel pair 413 instead of or may rest for a static measurement. Moreover, channels 406 within a given rotation may measure multiple phases. For example, some channels 406 of one or more channel pairs 412 in a rotation may measure hydrocarbon, while other channels 406 may measure the water in the same measurement rotation. Consequently, for large portions of downhole formation pump outs, it may be rare to find an entire rotation or set of channel measurements from one or more sensors that make a measurement for a single phase. In such instances, the conventional fluid analysis that uses a combination of channels from one or more samples to extract sample properties (chemical or physical) or a phase signature extraction may fail due to the multi-phase flow.

As disclosed herein, multi-channel selectivity (specificity for a given phase) may be greater than single channel sensitivity. Each phase signal may be an optical signal or a non-optical signal. In some examples, each channel 406 may be sensitive to a fluid phase, wherein each channel 406 may have a different response to a fluid phase by comparison to a non-fluid phase. Conversely, some channels 406 may not have high selectivity, but correlating with at least one additional channel 406 may increase selectivity of one or both the channels.

The current disclosure relates to the field challenges of dynamic sampling for fluid flow. As the fluid sample flows during the dynamic measurement of each rotation, channels 406 may meet different fluid phases. For example, the spectra of a plurality of common fluid samples 414 may be measured. as shown in FIG. 5.

Figure 5:
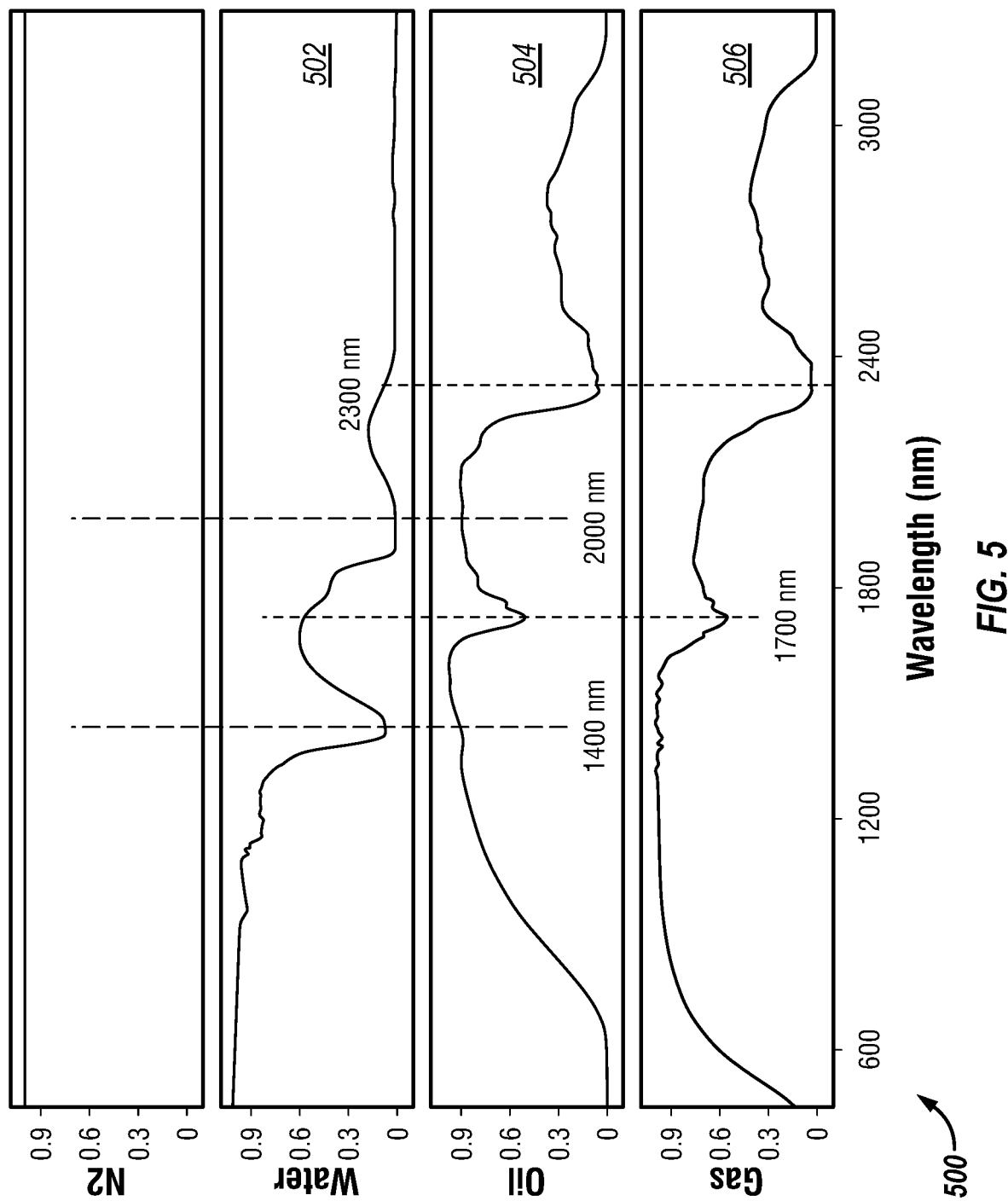
FIG. 5 depicts an optical spectra of different fluid samples.

FIG. 5 depicts the optical spectra 500 of different fluid samples. More specifically different optical absorbing characteristics of water 502, oil 504, and gas 506, as a function of wavelengths are depicted. Referring to FIG. 5, water 502 has absorbing peaks at the wavelength of 1400 nm and 2000 nm, while hydrocarbons 504, 506 have their absorbing peaks at a wavelength of 1700 nm and 2300 nm. More specifically, water 502 may have different amplitude responses when compared to hydrocarbons 504, 506 on the channels 406 in which their transfer covers characteristic wavelengths. For example, a phase signal near 1400 nm may have a weak amplitude for water 502, whereas the phase signal may have a stronger amplitude for hydrocarbons 504, 506. It should be noted that channel 406 phase signals may comprise single wavelengths or multiple wavelengths. Channels 406 may comprise embedded transmission functions. Conversely, in some instances channels 406 may not comprise embedded transmission functions. The feature depicted in FIG. 5 may contribute to the identification of hydrocarbons 504, 506 from water 502 or from gas 506 on each channel in multi-phase processes.

Fluid labeling may comprise determining a specific type of fluid, whereas the fluid may comprise oil, gas, or solids. Determining the fluid or the fluid composition may comprise identifying the phase of the particular cluster. The determination of a cluster's phase may include a priori knowledge of at least one of a plurality of non-optical sensor 348 (e.g., referring to FIG. 3), wherein non-optical sensor 348 may comprise density channels, aqueous channels, organic channels, and the like, and combinations thereof. It should be noted that a priori knowledge may include data from the field or laboratory data. In examples, non-optical sensor 348 may be closely positioned to the optical sensors 334. Nonetheless, in some examples, non-optical sensor 348 may not be closely positioned. In some examples, information obtained from non-optical sensors 348 may be used to assist in fluid labeling. Channels may also be grouped by synchronization, thus allowing increased sensitivity to allow time or distance separation, while still being grouped into a plurality of channels. Measurements from non-optical sensor 348 and channels 406 may be utilized together to label fluid 414 (e.g., referring to FIG. 4) that has been drawn out of a formation and into downhole fluid sampling tool 100.

Figure 6:
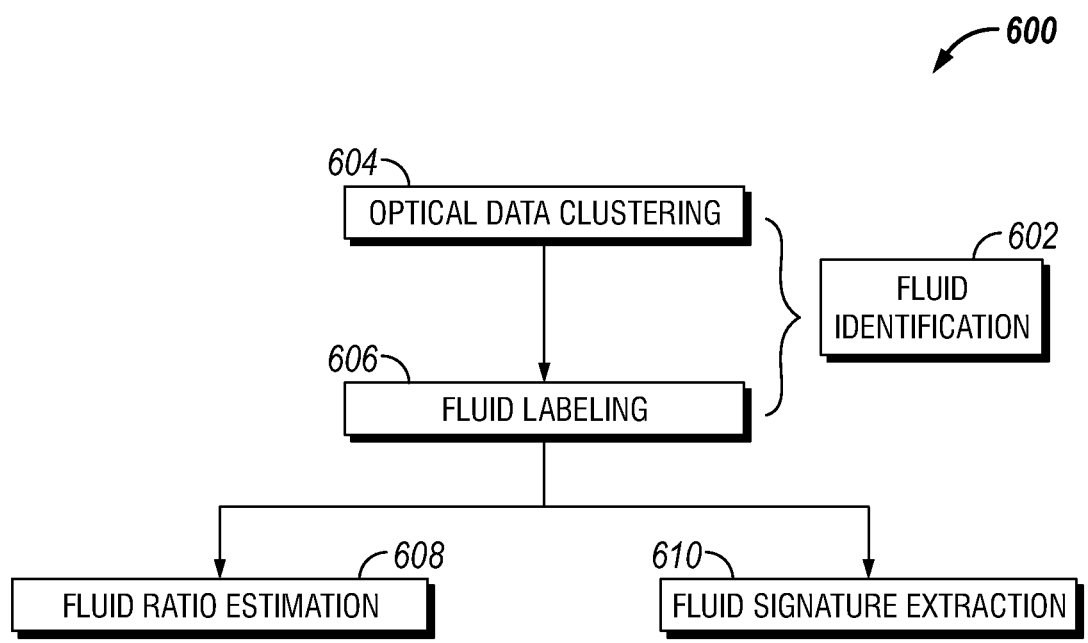
FIG. 6 depicts a workflow diagram for a multi-phase fluid analysis.

FIG. 6 depicts a workflow or flow diagram for multi-phase fluid analysis 600. A fluid identification 602 on a per channel 406 basis is completed before performing a fluid ratio estimation 608, a fluid signature extraction 610, or any physical or chemical properties are measured, estimated, and/or modeled. Fluid identification methods 602 disclosed herein may comprise at least two steps, wherein the at least two steps may comprise data clustering 604 and fluid labeling 610. Methods 602 disclosed herein may be applied to any set of multiple measurements from one or more sensors. Alternatively, the methods disclosed herein may be applied to any set of multiple measurements from at least one sensor, from one or more sensors, from two or more sensors, or from three or more sensors, etc. It should be noted the optical methods disclosed herein are exemplary methods.

During the optical data clustering step 604, the optical data may be separated into at least two groups, wherein the separation is based on amplitude responses on each channel 406. A threshold on a histogram may be easily found for most channels 406 whose passbands may be located near the characteristic wavelengths. However, in certain field cases, the hydrocarbons may be complicated mixtures, and water may not be pure water, wherein the water may comprise salts solids, organic compounds, or other substances. These complicated mixtures may increase the level of difficulty in finding a reasonable threshold on the histogram for certain channels.

Fluid labeling phases 606 may comprise at least two levels of computation. For example, fluid labeling 606 may comprise a fluid ratio extraction 608, wherein a volume extraction of the ratio of the phases may be determined. In addition, the labeling may comprise a fluid phase signal extraction 610. The fluid phase signal extraction 610 may be completed, wherein the phase signals are extracted and separated into at least two groups (not shown), such as Group 1 and Group 2. The two levels of computation may comprise computing the total amount of phase in Group 1 and also computing the total amount of phase in Group 2. It should be noted that phase signals may be separated into water (aqueous), oil (organic), gas, or solid phase signals. The separation of phase signals provides a resulting pure phase signal, thereby enabling the estimation of the phase, wherein a composition analysis may be run on the phase. This enables a multiphase composition analysis. In general, it should be noted that current systems are not designed for multi-phase composition analysis.

Figure 7A:
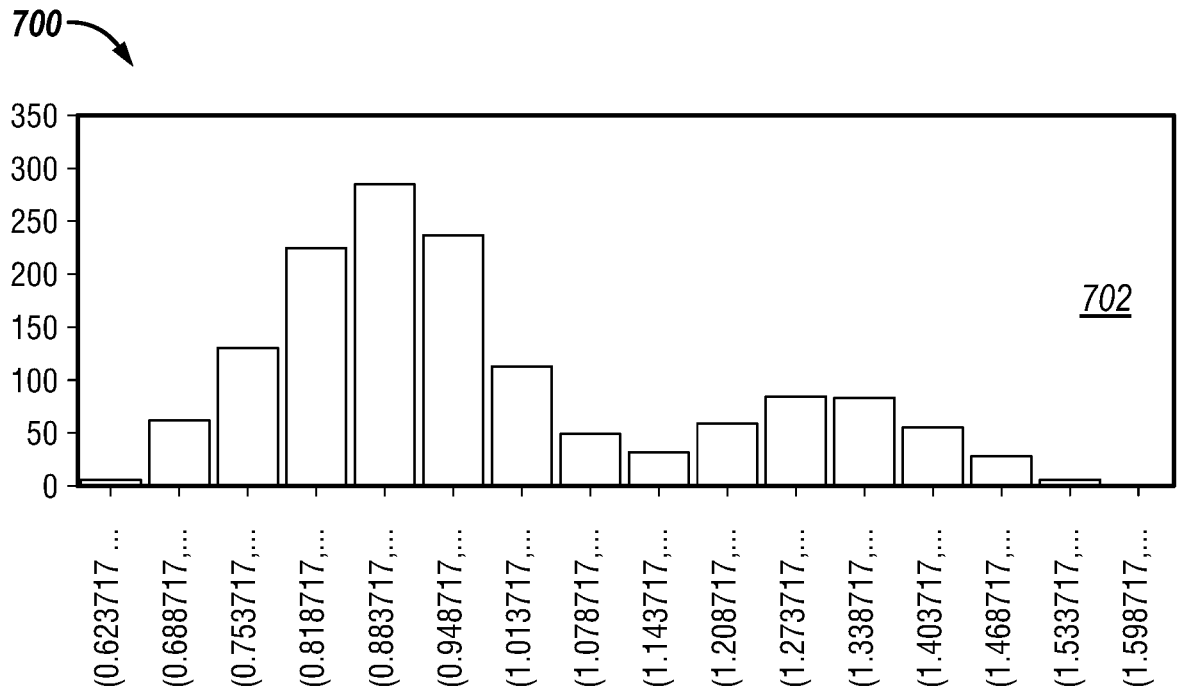
FIGS. 7A and 7B depict histograms for a channel pair on an optical observation of a simulated fluid flow.
Figure 7B:
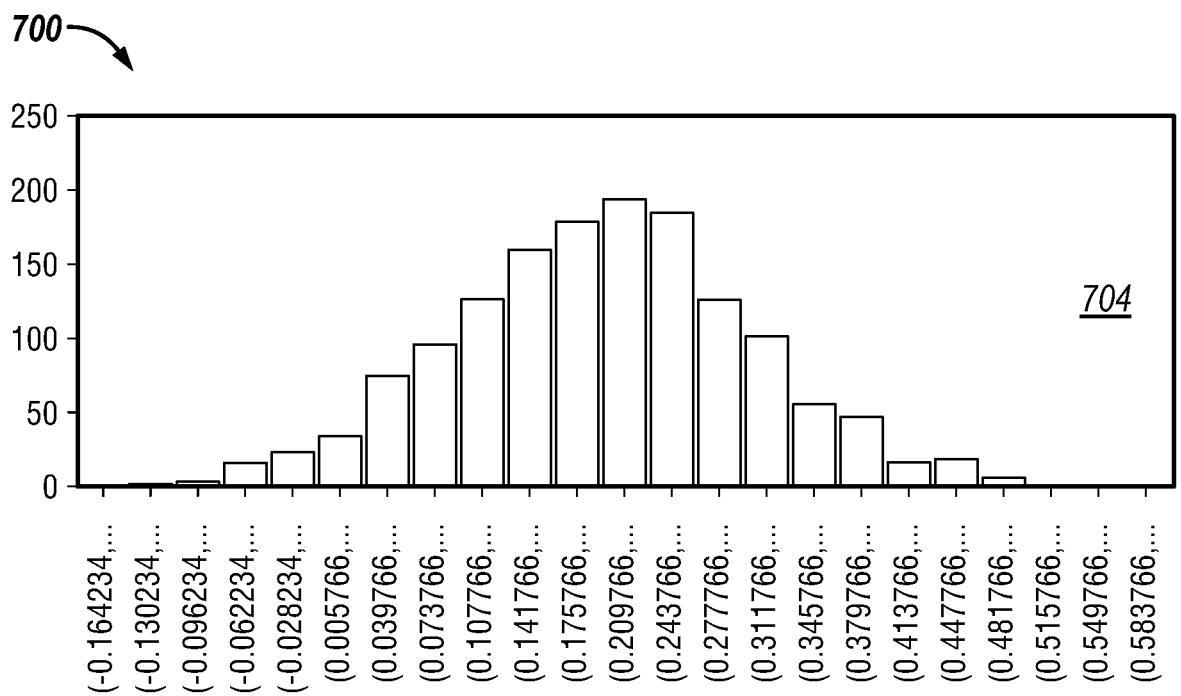

FIGS. 7A and 7B depicts histograms 700 for a channel pair on the optical observation of a simulated fluid flow. The two channels are in the same channel pair and measure the fluid sample simultaneously. However, due to the differences between their transfer functions, the above channel 702 may be easy for classification on its histogram, while bottom channel 704 may be difficult to separate. There are two prominent peaks on the histogram of the above-stated channel 702, wherein the two fluids may be easily separated. Referencing the bottom channel histogram 704, it is difficult to identify an effective threshold to separate the two fluids. Hence fluid grouping or clustering methods applied on single channels may present large classification errors that may lead to poor performance.

In order to overcome this challenge and improve the clustering performance, clustering may be performed on the two channels 406 of the active channel pair 413 (e.g., referring to FIG. 4). It should be noted that paring based on close pairs is also an option. Generally, bracketing with multiple channels may also be an option. Moreover, further distributions may be matched from a plurality of dissimilar sensors. Distributions may also be matched from a plurality of similar sensors. As the two paired channels 406 measure the fluid simultaneously, the dual-channel clustering may share the information between the paired channels 406, which may result in an improvement of overall performance.

Figure 8:
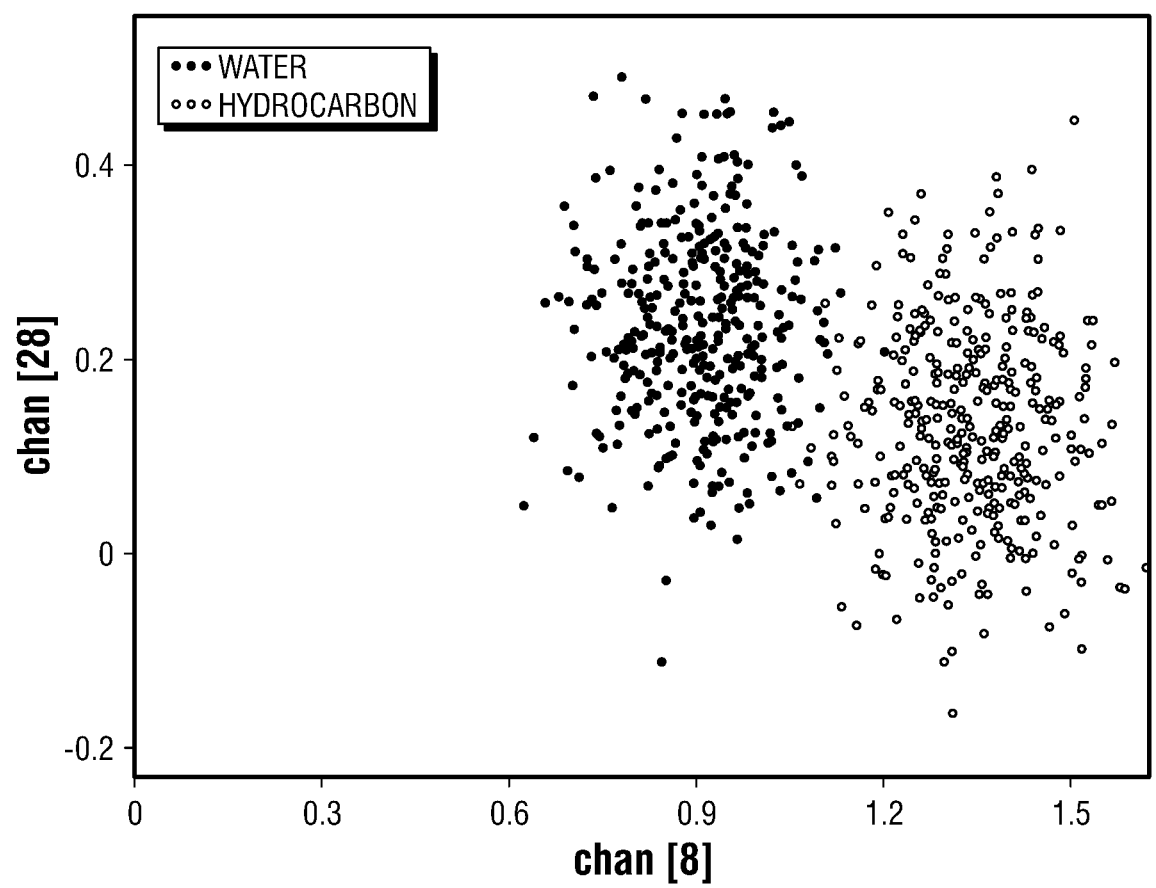
FIG. 8 depicts a 2D cross-plot of the channel pair depicted in FIG. 7. The information along the vertical direction is not suitable for classification.

For example, FIG. 8 depicts a 2D cross-plot 800 of the channel pair in FIGS. 7A and 7B. The information along the vertical direction may not be suitable for classification. The two kinds of fluids may essentially be isolated on the 2D cross-plots of the two channels. The information on the bottom channel may be insufficient for classification. The optical data on the 2D cross-plot may be more easily separated, benefitting from the information of the above channel. The incorporation of at least two channels, resulting in at least a dual channel classification, may allow information sharing between paired channels, which may subsequently improve the classification performance of at least two channels.

The optical data generated after clustering may be organized into two or more groups for each of the channel pairs. However, the fluid type for each of the two or more groups may comprise a single fluid or a plurality of fluids. As the signatures may be different among the channels, wherein the subsurface fluid samples may be complicated, it may become challenging to determine the fluid type for the clustered groups on each channel pair using only the optical observations. In some cases, optical channels may be substantial enough to identify a pair as water, oil, or gas. Conversely, in other cases, third channel or third sensor information may be used. In other examples, a partial fingerprint may be comprised of the optical data and tested against histogram properties of other channels.

In some examples, the observed density information may be used as a guide to assist the fluid labeling for the classified optical data. In such configurations, density may be observed to be located close to the target sensor for the purpose of observing the same distribution of fluid, if not spatially or temporally collocated. Therefore, the densitometer may see the same multimodal or sufficiently similar multimodal distribution as an optical sensor (or other target sensor for channel fluid typing).

Figure 9:
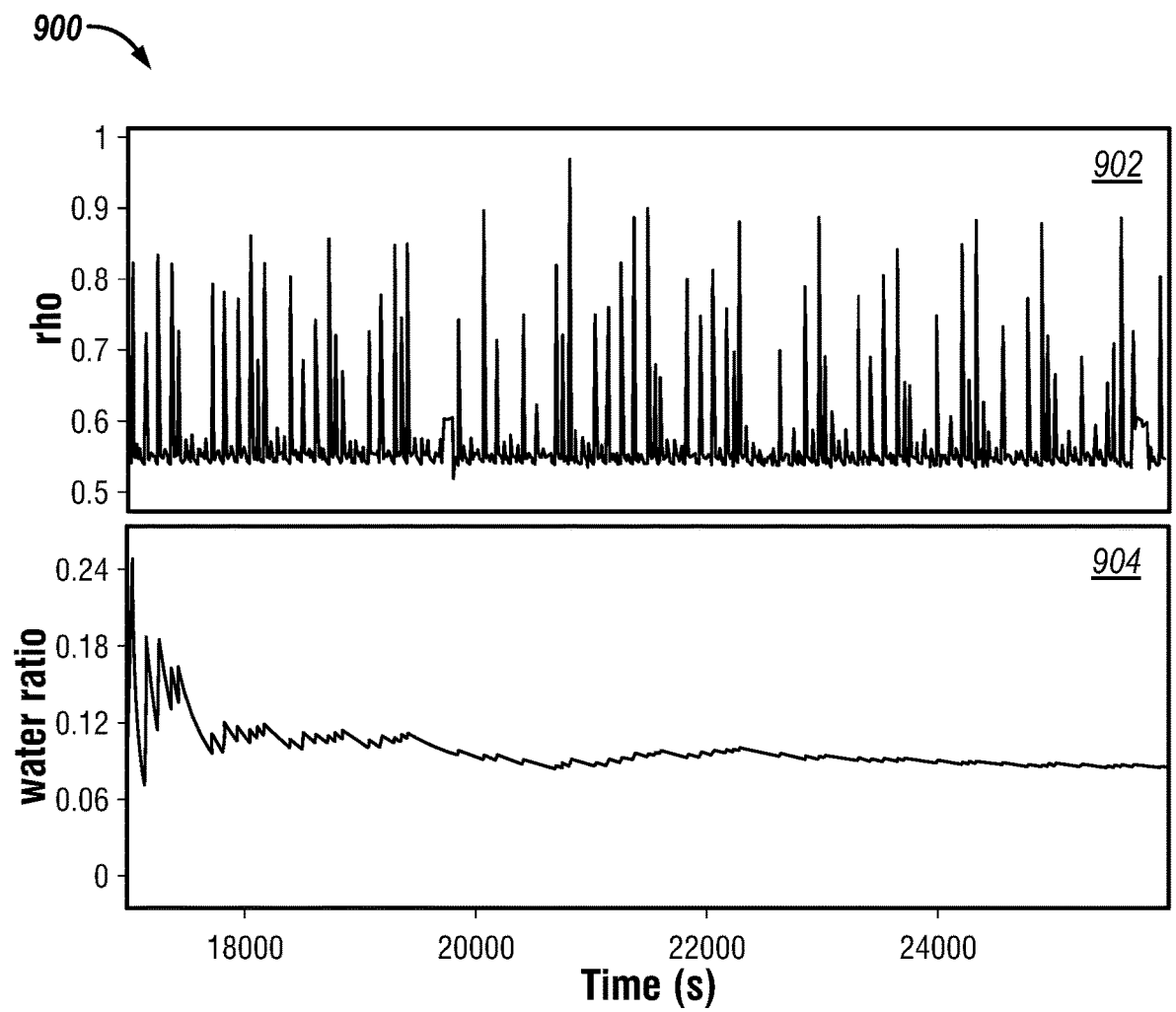
FIG. 9 depicts a density observation and the initial water ratio used as guide information for fluid labeling.

A method for density guided fluid labeling 606 (e.g., referring to FIG. 6) may comprise estimating initial density-based water ratio from density observation, as depicted in FIG. 9. FIG. 9 depicts the density observation 902 and the initial water ratio 904 used as guide information 900 for fluid labeling 606. It should be noted, the initial water ratio 608 may be estimated based on the density data. The method may further comprise determining a dominating fluid, wherein the dominating fluid may be water of a hydrocarbon fluid. The determining of the dominating fluid comprises determining a current water ratio. If the current water ratio is less than a threshold (at or about 0.5), then the dominating fluid is hydrocarbon. If the current water ratio is not less than a threshold, the dominating fluid is water. The method for density guided fluid labeling may further comprise labeling a first cluster group, wherein the first cluster group is the cluster group that has more samples with the dominating fluid. The method may further comprise labeling a second cluster group with another fluid type, wherein the second cluster group is the cluster group that has the least number of samples with the dominating fluid. For example, fluid labeling tries to label the fluids with two type: formation fluid or mud filtrate. If the dominating group is labelled as formation fluid, the other group will be labelled as mud filtrate, and vice versa.

Other methods for density guided fluid labeling may take the mode of the modes of the distributions, or tail characteristics of the modes of the distributions, as opposed to the total population of the modes as described above. It should be noted that if a single optical channel 406, or coupled optical channel 406 provides fluid phase identification, then it too may be used as a distribution modal reference. After the fluid is identified, an estimation of the ratio of each fluid 608 in a local window (given as parameter) may be determined.

Clustering is a technique of grouping the channels 408 according to a phase, whereas other methods may include pattern recognition, or pre-determined vector projections. Nonlinear methods, including but not limited to, neural network classification may also be appropriate. The histogram 700 may be performed on a small window. In some examples, the histogram 700 may be performed on a large window. The window may be fixed or variable. In some examples, the window may be anchored atop a specific region of the pump out, and, yet in the embodiments, the anchoring may change location. The window may remain unanchored. As the clustering is completed on each channel pair, the real-time fluid ratio may be obtained for each channel pair.

Figure 10:
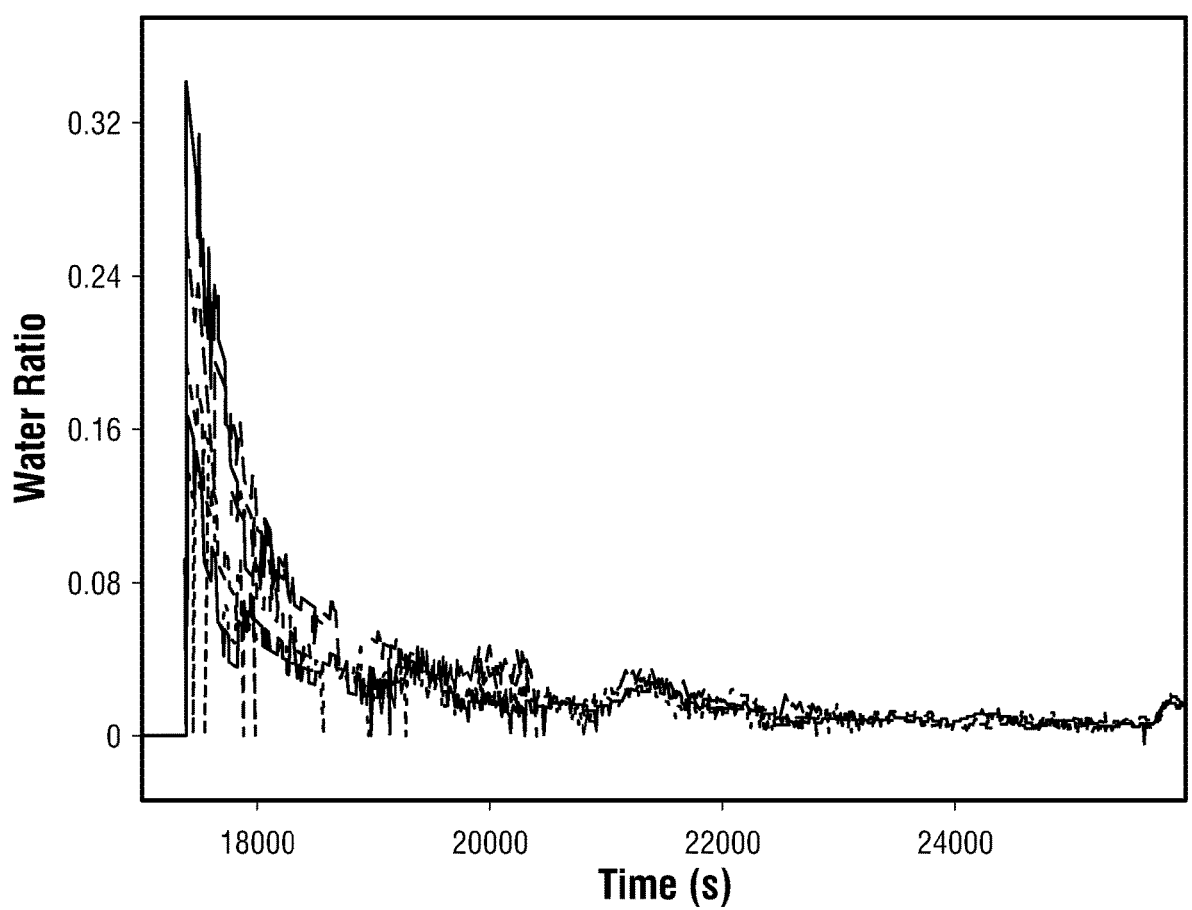
FIG. 10 depicts an example of an estimated water ratio for each channel pair of a field optical observation.

FIG. 10 depicts an example of an estimated water ratio for each channel pair of a field optical observation. FIG. 10 shows the decreasing trend of the water in the mud during the build-up process. For example, at the beginning, the water ratio estimation among different channel pairs may not be consistent due to the shortage of data observed. Nonetheless, as time progresses, the fluid ratio estimations 608 of all the channel pairs 412 may become consistent. It should be noted that in addition to suitable optical channels or combinations of optical channels 406, and/or a density sensor, a capacitance sensor, resistivity sensor, or acoustic sensor may also provide good reference for fluid identification 602.

An algorithm or method for obtaining a real time signature for hydrocarbon may comprise allocating memory for hydrocarbon signature of all channels. The method may further comprise initializing the signature with the observed multiphase measurements; and replacing the signature of each channel with the observed amplitude if the dominating fluid is hydrocarbon. The method may further comprise outputting the real time signature for each sampling circle.

Figure 11:
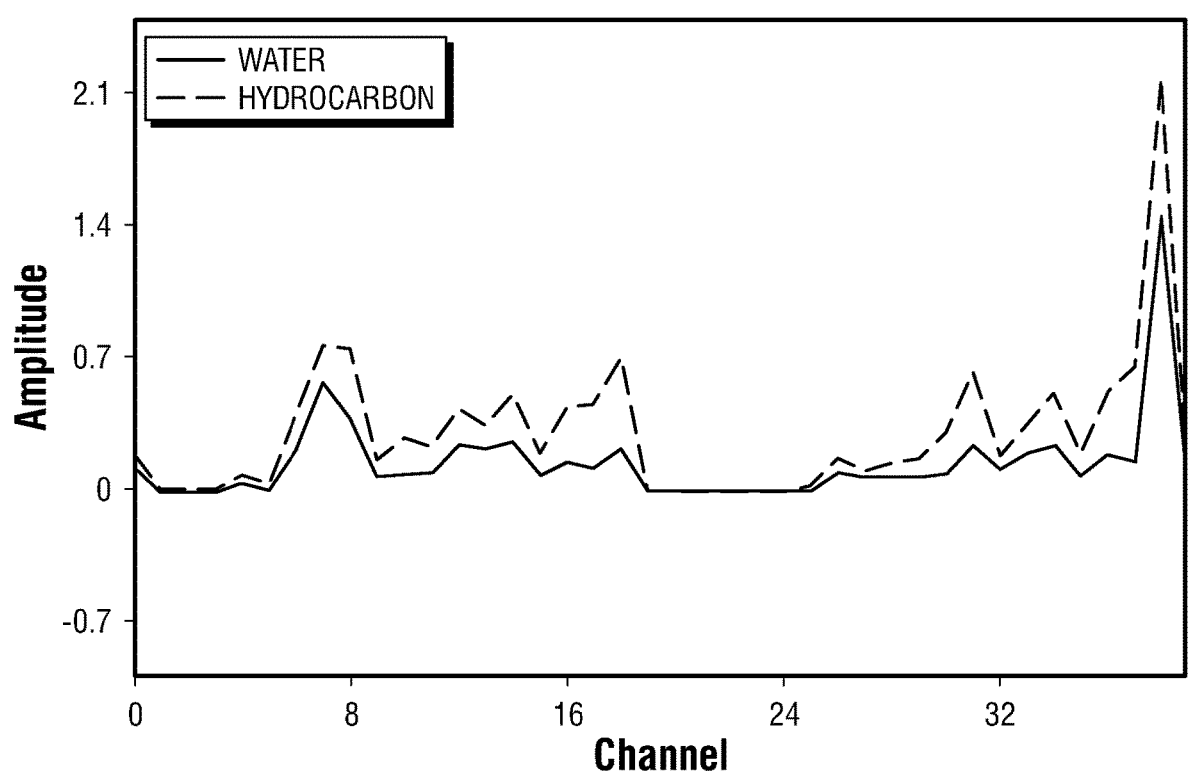
FIG. 11 depicts a real time hydrocarbon signature at a sampling circle for field optical data.

FIG. 11 depicts a real time hydrocarbon signature at one sampling circle for field optical data. This depiction may include the separated optical information, the pure signatures of formation hydrocarbon fluids, and mud water fluids. After determining the pure hydrocarbon and the pure water signatures, combined signatures of hydrocarbon and water may be constructed, following an estimated real time water ratio.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

Statement 1: A method for measuring downhole fluid properties may comprise disposing a downhole fluid sampling tool into a wellbore. The downhole fluid sampling tool may comprise at least one probe configured to fluidly connect the downhole fluid sampling tool to a formation in the wellbore and at least one passageway that passes through the at least one probe and into the downhole sampling tool. The method may further comprise drawing a wellbore fluid through the at least one probe and through the at least one passageway, obtaining a first channel measurement of the wellbore fluid with at least one sensor that is fluidly coupled to the at least one passageway, obtaining at least a second channel measurement from the at least one sensor, clustering channel data from a plurality of channel measurements comprising the first channel measurement and the at least second channel measurement, and measuring a phase through a plurality of channels. The method may further comprise separating a plurality of phase signals based on the phase measured through the plurality of channels, labeling the wellbore fluid based at least in part on the plurality of phase signals, assigning the plurality of phase signals to specific phases of a multi-phase fluid, and estimating a fluid property of the wellbore fluid.

Statement 2. The method of statement 1, wherein the at least one sensor is an optical fluid sensor.

Statement 3. The method of statement 1, wherein the at least one sensor is a non-optical fluid sensor.

Statement 4. The method of any preceding statements 1-3, wherein the plurality of channels are positioned together.

Statement 5. The method of any preceding statements 1-3, wherein the plurality of channels are synchronized.

Statement 6. The method of any preceding statements 1-5 wherein the fluid property comprises compositional component concentrations comprising methane, ethane, propane, butane, pentane, or combinations thereof.

Statement 7. The method of any preceding statements 1-6, wherein the fluid property comprises organic liquid components comprising a hexane plus fraction, saturates fraction, aromatics fraction, resins fraction, asphaltenes fraction, or combinations thereof.

Statement 8. The method of any preceding statements 1-7, wherein the fluid property is a physical property selected from the group consisting of compressibility, density, thermal conductivity, heat capacity, viscosity, bubble point, gas to oil ration, phase envelope for gas-liquid, phase envelope for solid-liquid, or combinations thereof.

Statement 9, The method of any preceding statements 1-8, further comprising identifying pure phase channel observations versus mixed phased channel observations for each of the plurality of channels.

Statement 10. The method of any preceding statements 1-9, further comprising identifying the phases of a dominating fluid for each of the plurality of channels.

Statement 11. The method of statement 10, wherein identifying the phases of the dominating fluid comprises determining a current water ratio.

Statement 12. The method of statement 11, wherein the dominating fluid is hydrocarbon when the current water ratio is less than a threshold.

Statement 13. The method of statement 11, wherein the dominating fluid is water when the current water ratio is not less than a threshold.'

Statement 14. The method of statement 10, wherein labeling the fluid further comprises labeling a first cluster group, wherein the first cluster group is the cluster group that has more samples with the dominating fluid.

Statement 15. The method of statement 14, further comprising labeling a second cluster group with another fluid type, wherein the second cluster group is the cluster group that has the least number of samples with the dominating fluid.

Statement 16. A system may comprise a downhole fluid sampling tool. The downhole fluid sampling tool may comprise at least one probe configured to fluidly connect the downhole fluid sampling tool to a formation in the wellbore, at least one passageway that passes through the at least one probe and into the downhole sampling tool, and at least one sensor that is fluidly couple to the at least one passageway and configured to take a first channel measurement and at least a second channel measurement of a wellbore fluid that is drawn from the formation and through the at least one passageway. The system may further comprise an information handling system configured to cluster channel data from a plurality of channel measurements comprising the first channel measurement and the at least second channel measurement, measure a phase through a plurality of channels, separate a plurality of phase signals based on the phase measured through the plurality of channels, label the wellbore fluid based at least in part on the plurality of phase signals, assign the plurality of phase signals to specific phases of a multi-phase fluid, and estimate a fluid property of the wellbore fluid.

Statement 17. The system of statement 16, wherein the at least one sensor is an optical fluid sensor.

Statement 18. The method of any preceding statements 16 or 17, wherein the at least one sensor is a non-optical fluid sensor.

Statement 19. The method of any preceding statements 16-18, wherein the plurality of channels are positioned together.

Statement 20. The method of s any preceding statements 16-19, wherein the plurality of channels are synchronized.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method for measuring downhole fluid properties, comprising:
    disposing a downhole fluid sampling tool into a wellbore wherein the downhole fluid sampling tool comprises:
        at least one probe configured to fluidly connect the downhole fluid sampling tool to a formation in the wellbore; and
        at least one passageway that passes through the at least one probe and into the downhole sampling tool;
    drawing a wellbore fluid through the at least one probe and through the at least one passageway;
    obtaining a first channel measurement of the wellbore fluid with at least one sensor that is fluidly coupled to the at least one passageway;

obtaining at least a second channel measurement from the at least one sensor, wherein the at least one sensor is an optical fluid sensor;

clustering channel data from a plurality of channel measurements comprising the first channel measurement and the at least second channel measurement, wherein the first channel and the at least second channel are active optical channel pair measuring the wellbore fluid simultaneously at different wavelength;

measuring a phase through a plurality of channels;

separating a plurality of phase signals based on the phase measured through the plurality of channels;

labeling the wellbore fluid based at least in part on the plurality of phase signals;

assigning the plurality of phase signals to specific phases of a multi-phase fluid; and estimating a fluid property of the wellbore fluid.

2. The method of claim 1, wherein the plurality of channels are positioned together.

3. The method of claim 1, wherein the plurality of channels are synchronized.

4. The method of claim 1, wherein the fluid property comprises compositional component concentrations comprising methane, ethane, propane, butane, pentane, or combinations thereof.

5. The method of claim 1, wherein the fluid property comprises organic liquid components comprising a hexane plus fraction, saturates fraction, aromatics fraction, resins fraction, asphaltenes fraction, or combinations thereof.

6. The method of claim 1, wherein the fluid property is a physical property selected from the group consisting of compressibility, density, thermal conductivity, heat capacity, viscosity, bubble point, gas to oil ration, phase envelope for gas-liquid, phase envelope for solid-liquid, or combinations thereof.

7. The method of claim 1, further comprising identifying pure phase channel observations versus mixed phased channel observations for each of the plurality of channels.

8. The method of claim 1, further comprising identifying the phases of a dominating fluid for each of the plurality of channels.

9. The method of claim 8, wherein identifying the phases of the dominating fluid comprises determining a current water ratio.

10. The method of claim 9, wherein the dominating fluid is hydrocarbon when the current water ratio is less than a threshold.

11. The method of claim 9, wherein the dominating fluid is water when the current water ratio is not less than a threshold.

12. The method of claim 8, wherein labeling the fluid further comprises labeling a first cluster group, wherein the first cluster group is the cluster group that has more samples with the dominating fluid.

13. The method of claim 12, further comprising labeling a second cluster group with another fluid type, wherein the second cluster group is the cluster group that has the least number of samples with the dominating fluid.

14. A system comprising:
a downhole fluid sampling tool comprising:
at least one probe configured to fluidly connect the downhole fluid sampling tool to a formation in the wellbore;
at least one passageway that passes through the at least one probe and into the downhole sampling tool; and
at least one sensor that is fluidly couple to the at least one passageway and configured to take a first channel measurement and at least a second channel measurement of a wellbore fluid that is drawn from the formation and through the at least one passageway, wherein the at least one sensor is an optical fluid sensor; and
an information handling system configured to:
cluster channel data from a plurality of channel measurements comprising the first channel measurement and the at least second channel measurement, wherein the first channel and the at least second channel are active optical channel pair measuring the wellbore fluid simultaneously at different wavelength;
measure a phase through a plurality of channels;
separate a plurality of phase signals based on the phase measured through the plurality of channels;
label the wellbore fluid based at least in part on the plurality of phase signals;
assign the plurality of phase signals to specific phases of a multi-phase fluid; and
estimate a fluid property of the wellbore fluid.

15. The system of claim 14, wherein the plurality of channels are positioned together.

16. The system of claim 14, wherein the plurality of channels are synchronized.

17. A method for measuring downhole fluid properties, comprising:
disposing a downhole fluid sampling tool into a wellbore wherein the downhole fluid sampling tool comprises:
at least one probe configured to fluidly connect the downhole fluid sampling tool to a formation in the wellbore; and
at least one passageway that passes through the at least one probe and into the downhole sampling tool;
drawing a wellbore fluid through the at least one probe and through the at least one passageway;
obtaining a first channel measurement of the wellbore fluid with at least one sensor that is fluidly coupled to the at least one passageway;
obtaining at least a second channel measurement from the at least one sensor, wherein the at least one sensor is an optical fluid sensor;
clustering channel data from a plurality of channel measurements comprising the first channel measurement and the at least second channel measurement, wherein the first channel and the at least second channel are active optical channel pair measuring the wellbore fluid simultaneously;
measuring a phase through a plurality of channels;
separating a plurality of phase signals based on the phase measured through the plurality of channels;
labeling the wellbore fluid based at least in part on the plurality of phase signals;
assigning the plurality of phase signals to specific phases of a multi-phase fluid; and
estimating a fluid property of the wellbore fluid.

* * * * *